United States Patent
Marcano et al.

(10) Patent No.: US 11,198,871 B2
(45) Date of Patent: Dec. 14, 2021

(54) RIBOSWITCH-MEDIATED REGULATORY CONTROL OF GENE EXPRESSION IN THERMOPHILIC BACTERIA

(71) Applicant: Alliance for Sustainable Energy, LLC, Golden, CO (US)

(72) Inventors: Joan Gabriel Marcano, Denver, CO (US); Katherine Jenyan Chou, Lakewood, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 16/792,761

(22) Filed: Feb. 17, 2020

(65) Prior Publication Data

US 2020/0263177 A1    Aug. 20, 2020

Related U.S. Application Data

(60) Provisional application No. 62/806,407, filed on Feb. 15, 2019.

(51) Int. Cl.
| | |
|---|---|
| *C12N 15/74* | (2006.01) |
| *C12N 15/113* | (2010.01) |
| *C12P 7/06* | (2006.01) |

(52) U.S. Cl.
CPC ............ *C12N 15/113* (2013.01); *C12P 7/065* (2013.01)

(58) Field of Classification Search
CPC ........ C12N 15/74; C12N 15/113; C12P 7/065
See application file for complete search history.

(56) References Cited

PUBLICATIONS

Marcano-Velázquez et al., "Structure-guided mutational analysis of gene regulation by the Bacillus subtilis pbuE adenine-responsive riboswitch in a cellular context", The Journal of Biological Chemistry, Feb. 2015, vol. 290, No. 7, pp. 4464-4475.

Marcano-Velázquez et al., "Developing Riboswitch-Mediated Gene Regulatory Controls in Thermophilic Bacteria", ACS Synthetic Biology, Apr. 2019, vol. 8, No. 4, pp. 633-640.

Mearls et al., "Development of a regulatable plasmid-based gene expression system for Clostridium thermocellum", Applied Genetics Microbiology and Biotechnology, 2015, vol. 99, No. 18, pp. 7589-7599.

*Primary Examiner* — Tekchand Saidha
(74) *Attorney, Agent, or Firm* — Sam J. Barkley

(57) ABSTRACT

Methods of riboswitch-mediated gene expression in thermophiles are provided herein.

6 Claims, 11 Drawing Sheets

Specification includes a Sequence Listing.

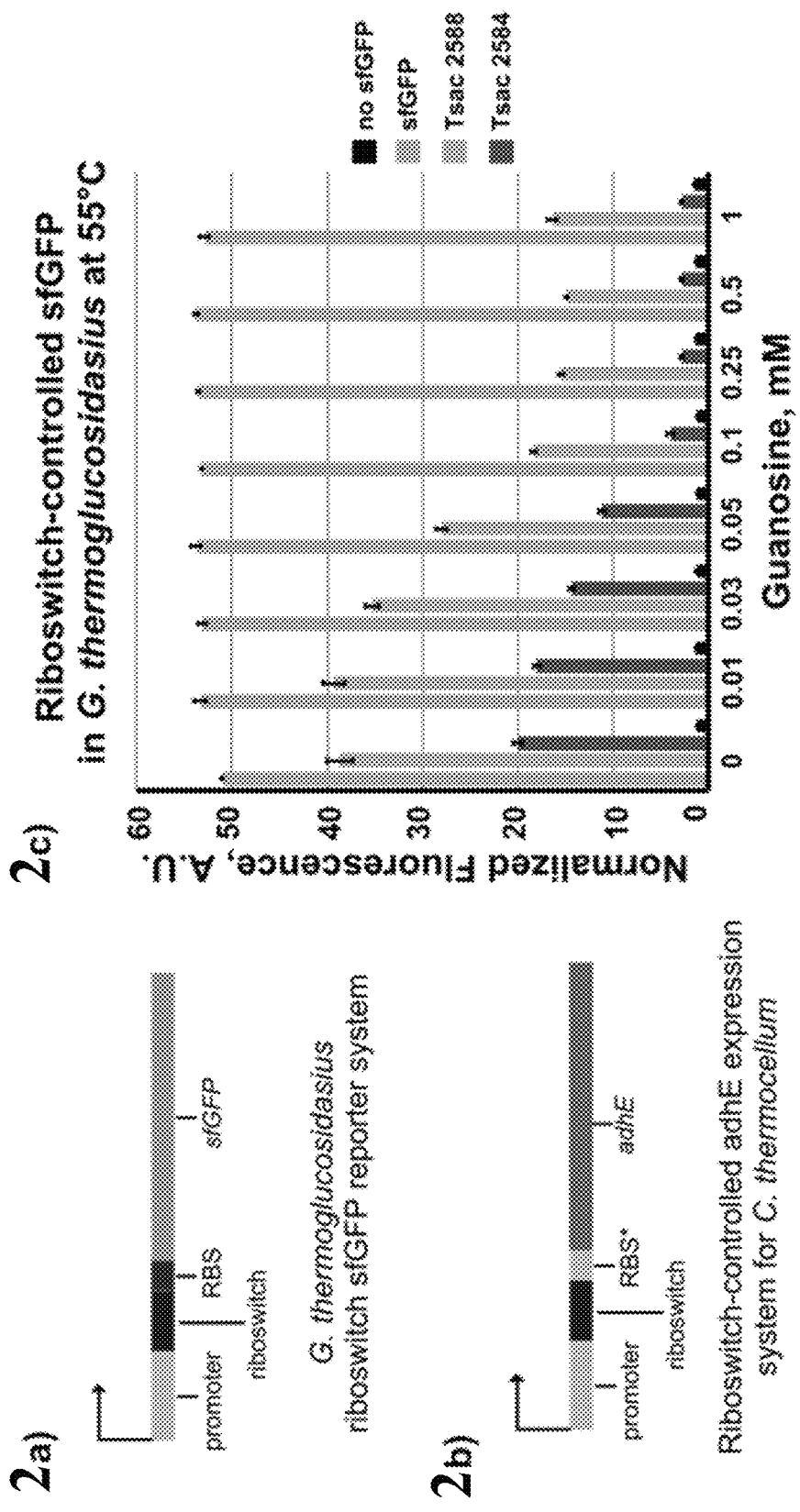
FIGs. 2a, 2b, and 2c

FIGs. 7a, 7b, 7c, and 7d

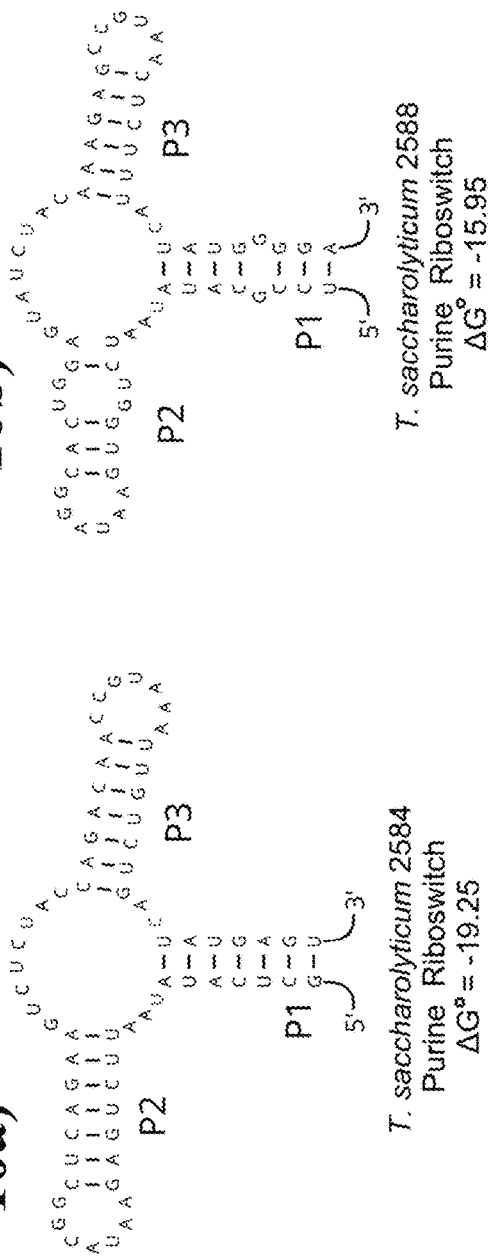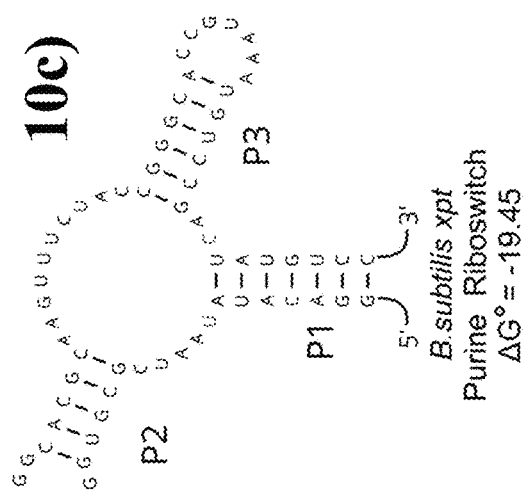
FIG. 10

RIBOSWITCH-MEDIATED REGULATORY CONTROL OF GENE EXPRESSION IN THERMOPHILIC BACTERIA

CROSS-REFERENCE TO RELATED APPLICATIONS

This application claims priority under 35 U.S.C. § 119 to U.S. Provisional Patent Application No. 62/806,407 filed on 15 Feb. 2019, the contents of which are hereby incorporated by reference in their entirety.

CONTRACTUAL ORIGIN

The United States Government has rights in this invention under Contract No. DE-AC36-08GO28308 between the United States Department of Energy and the Alliance for Sustainable Energy, LLC., the Manager and Operator of the National Renewable Energy Laboratory.

BACKGROUND

Thermophilic bacteria are attractive hosts for the production of bio-based chemicals. While various genetic manipulations have been performed in the metabolic engineering of thermophiles, a robust means to regulate gene expression in these bacteria (existing in temperatures at around 55° C.) has been, hitherto, missing.

SUMMARY

In an aspect, disclosed herein is a non-naturally occurring riboswitch operably linked to a promoter wherein the riboswitch is capable of regulating the expression of a gene of interest in a non-naturally occurring thermophilic organism. In an embodiment, the non-naturally occurring riboswitch has a nucleotide sequence that is greater than 85% identical to SEQ ID NO: 1. In an embodiment, the non-naturally occurring riboswitch has a nucleotide sequence that is greater than 85% identical to SEQ ID NO: 3. In another embodiment, the non-naturally occurring riboswitch is capable of regulating the expression of a gene of interest at temperatures greater than 50 degrees Celsius. In an embodiment, the non-naturally occurring riboswitch causes the expression of the gene of interest to be downregulated. In an embodiment, the non-naturally occurring riboswitch causes the expression of the gene of interest to be upregulated. In an embodiment, the non-naturally occurring riboswitch causes the gene of interest to be expressed up to 29-fold over wild-type expression. In an embodiment, the gene of interest is adhE.

In an aspect, disclosed herein is method for regulating the expression of a gene of interest in a non-naturally occurring thermophilic organism comprising operably linking a non-naturally occurring riboswitch to an operator of the gene of interest wherein the expression of the gene of interest is regulated by adding a ligand to the non-naturally occurring thermophilic organism wherein the ligand binds to the non-naturally occurring riboswitch and regulates the expression of the gene of interest. In an embodiment, the binding of the ligand to the non-naturally occurring riboswitch downregulates the expression of the gene of interest. In an embodiment, the gene of interest is not expressed. In an embodiment, the binding of the ligand to the non-naturally occurring riboswitch upregulates the expression of the gene of interest. In an embodiment, the gene of interest is expressed up to 29-fold over wild-type expression levels. In an embodiment, the ligand is guanosine or 2-aminopurine. In an embodiment, the non-naturally occurring riboswitch consists of a nucleotide sequence that is at least 85% identical to SEQ ID NO: 1. In an embodiment, the non-naturally occurring riboswitch consists of a nucleotide sequence that is at least 85% identical SEQ ID NO: 3. In an embodiment, the gene of interest is adhE.

In an aspect disclosed herein is a method for making ethanol using a thermophilic organism comprising the steps of operably linking a non-naturally occurring riboswitch to an alcohol and aldehyde dehydrogenase and inducing the expression of the alcohol and aldehyde dehydrogenase by adding a ligand to the organism wherein the ligand binds to the non-naturally occurring riboswitch allowing for the expression of the alcohol and aldehyde dehydrogenase. In an embodiment, the thermophilic organism makes ethanol at temperatures greater than 50 degrees Celsius. In an embodiment, the organism makes ethanol at concentrations up to about 18 mM.

BRIEF DESCRIPTION OF THE DRAWINGS

FIG. 2a depicts a schematic diagram showing the design of the genetic elements measured by sfGFP in *G. thermoglucosidasius*. The promoter, RBS, and sfGFP are parts of the parental plasmid pG1AK. FIG. 2b depicts a riboswitch construct designed to regulate the adhE gene expression in *C. thermocellum*. The *RBS is composed of the native 21 nucleotides upstream of the ATG of gene Clo1314_2638 in *C. thermocellum* FIG. 2c depicts the regulatory response of the two *T. saccharolyticum* purine riboswitches using sfGFP as a reporter in *G. thermoglucosidasius*. Guanosine was used instead of guanine due to its higher solubility and its previously shown ability to affect purine riboswitches in gram-positive bacteria.

FIG. 3a depicts normalized fluorescence level in cultures with increasing concentrations of 2-AP.

FIG. 10a depicts the secondary structure of a purine riboswitch in *T. saccharolyticum*. FIG. 10b depicts the secondary structure of a purine riboswitch in *T. saccharolyticum*. As depicted in FIG. 10a and FIG. 10b, the riboswitch sequences identified in *T. saccharolyticum* contain the canonical structure of the purine riboswitch aptamer which is composed of a three-way junction surrounded by three paired regions P1, P2, and P3. The aptamer domain structure of the *B. subtilis* purine riboswitch is provided for comparison. As depicted in FIG. 10b, the aptamer domain of the of the Tsac 2588 riboswitch contains a bulge in the P2 region. This could be related to its differential regulatory activity compared to the Tsac 2584 riboswitch, as depicted in FIG. 10a. Nucleotides in red dictate the binding specificity of the purine riboswitches. From 5' to 3', if the sequence of these 3 nucleotides is U,U,C the aptamer domain bind specifically guanine. If the sequence is U,U,U, then the aptamer domain binds adenine. The folding energies for the secondary structure were calculated using the mFOLD software version 3.6 at 37° C. The structure of the pbuE riboswitch from *B. subtilis* is depicted in FIG. 10c.

DETAILED DESCRIPTION

Thermophilic and anaerobic bacteria are attractive hosts for the industrial production of high-valued chemicals. Higher fermentation temperatures (i.e., 55-60° C.) lead to faster feedstock conversion rates, reduce contamination in the bioreactors with ambient microorganisms, reduces the cooling costs associated with the biomass pretreatment steps, and make thermophiles favorable platform organisms in a sustainable bio-based economy. Various genetic engineering approaches have been implemented in thermophilic bacteria for the production of target chemicals at high titers. These approaches include targeted gene deletions, replacement, and insertions that aim to redirect the carbon and electron flux towards the desired product. In addition, the expression of non-native metabolic pathways have been introduced to thermophiles to generate compounds like isobutanol, or even expand their carbon source utilization. Reliable and characterized genetic "parts" such as promoters, ribosomal binding sites, and gene regulatory elements are useful in the strain engineering toward the desired phenotype. Such tools are readily available for model organisms such as *Escherichia coli* and *Saccharomyces cerevisiae*. However, finely tunable gene expression is largely missing in thermophilic bacteria. Characterized regulatable promoters using native inducers like xylose can unintendedly regulate additional endogenous genes and others such as the laminaribiose promoter require an expensive inducer molecule. Furthermore, up- or down-regulations of a gene may be required to fundamentally understand the gene functions when knock-ins and knock-outs are not viable. Thus, in an embodiment, disclosed herein are methods to identify and establish genetic components that regulate gene expression in thermophilic bacteria. These tools also assist in elucidating the physiology of thermophiles as well as enabling additional genome engineering approaches including CRISPR-cas9.

Figure 1A:
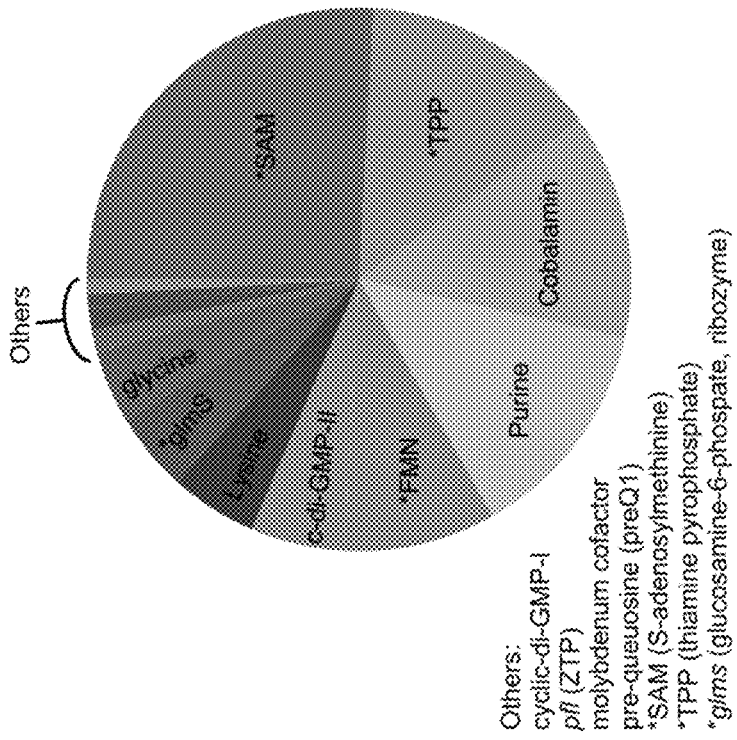
FIG. 1a depicts an example of a transcriptional "off" riboswitch mechanism of transcription termination.

Riboswitches are mRNA leader sequences that can regulate gene expression upon binding to a small molecule as a ligand. They are composed of two domains, the aptamer and the expression platform (see FIG. 1A). The aptamer domain folds into a structure that creates a high affinity binding pocket to selectively bind to the ligand. The expression platform mediates the gene expression by forming transcriptional terminators or preventing protein translation by secluding the ribosomal binding site.

The natural riboswitch aptamers have evolved to recognize a wide variety of ligands such as nucleotide derivatives, co-factors, amino acids, ions, and others. Riboswitches have been repurposed in various species to alter gene expression and as biosensors to monitor the concentration of natural intracellular compounds. Furthermore, a riboswitch can be adapted to recognize orthogonal ligands by mutagenesis of its binding pocket thereby expanding the molecules it recognizes. In an embodiment, these riboswitch variants may regulate multiple individual genes in response to different ligands in parallel. In addition, it is possible to generate novel RNA aptamers by artificial evolution and then couple them to natural expression platform to create functionally new riboswitches. These applications make riboswitches attractive regulators for the development of inducible and repressible genetic systems in thermophiles.

In an embodiment, disclosed herein is a comprehensive analysis of riboswitch distribution in thermophilic bacteria which indicates their significance in regulatory roles in thermophilic bacteria. The reporter assay disclosed herein rapidly characterizes riboswitch activity at elevated temperatures and serves as a platform to assess rationally engineered synthetic riboswitches' activity. An advantage to the methods used and non-naturally occurring organisms disclosed herein is that inexpensive and finely tunable gene expression enables basic studies of the species. Using methods disclosed herein allows for dynamic control of gene expression and strain engineering in thermophilic organisms amongst others. Disclosed herein is the first inducible and repressible gene regulatory systems using lower-priced orthogonal inducers and repressors in thermophiles, including *C. thermocellum*.

A bioinformatic search for various riboswitches in thermophilic bacteria revealed that major classes of riboswitches are present, suggesting the riboswitches' regulatory roles in these bacteria. By building synthetic constructs incorporating natural and engineered purine riboswitch sequences originating from exogenous, foreign species, the respective riboswitches' activities were quantified in repressing and upregulating gene expression. In an embodiment, the riboswitches' activities were investigated in *Geobacillus thermoglucosidasius* by using a green fluorescence protein. The elicited regulatory response was ligand-concentration-dependent. It was further demonstrated that riboswitch-mediated gene expression of adhE (responsible for ethanol production) in *C. thermocellum* can differentially restore ethanol production and cell growth in the adhE knockout mutant. Thus, in an embodiment, disclosed herein are methods for tunable gene expression that are useful across different thermophiles for broad applications including CRISPR-Cas9, for example.

Previously, the only in-vivo characterization of riboswitch activity at an elevated temperature is based on a fluoride riboswitch in the archaea *Thermococcus kodakarensis* which can grow in the range of 60°-100° C. The transcription and translation machineries for archaeal species is more akin to eukaryotic systems, and thus, those systems are not useful in thermophilic bacteria. In an embodiment, plasmid-based synthetic constructs were designed and built that incorporated both natural and engineered riboswitch sequences that originated from exogenous, bacteria. The activity of the engineered riboswitches was measured using a green fluorescence protein known to function at elevated temperatures (up to 70° C.). Also assessed was the riboswitch-dependent tuning of a gene responsible for ethanol production (adhE) in *Clostridium thermocellum*. Presented herein is the first in-vivo characterization of riboswitches at 55° C. which allows for the use of mesophilic riboswitches to regulate gene expression in thermophiles.

Figure 1B:
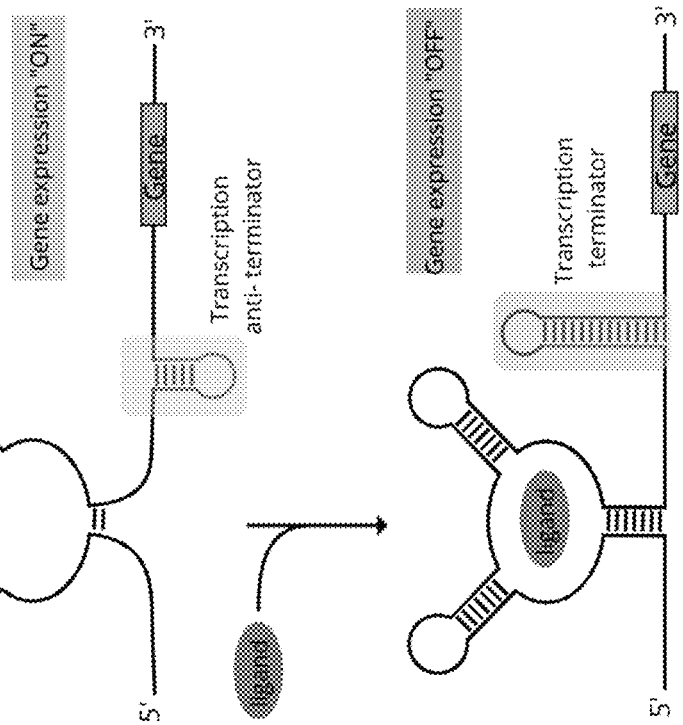
FIG. 1b depicts the distribution of 961 riboswitch sequences identified using INFERNAL in 78 representative thermophilic bacterial genomes.

Previous bioinformatics analyses had uncovered that riboswitches are present throughout the majority of bacterial clades. However, no study has focused on the diversity and distribution of riboswitch sequences specifically in thermophilic bacteria. Using the INFERNAL software package, which utilizes covariance models (CMs) built with the RNA sequence and structural conservation, 961 unique riboswitch sequences were identified among 78 thermophilic genomes analyzed from the RefSeq database (see FIG. 1B). Only five of the analyzed genomes, including *Hydrogenobacter* and *Hydrogenobaculum*, do not contain riboswitches. Of the twenty-five types of riboswitch searched with the CM models, only seventeen were detected leaving eight types of riboswitches not detected in any of the analyzed genomes. Notably, the riboswitches that were not found in the thermophilic genomes correspond to variants of S-adenosylmethionine and pre-quenosine-1 (preQ1) riboswitches which also occur in low frequencies among general bacterial databases.

Results disclosed herein show that major classes of riboswitches are present in thermophiles and the relative abundance of each class resembles those observed for all bacterial classes. The genomes that were characterized as thermophilic are for organisms that have an optimal growth temperature greater than 50° C. Without being bound by theory, this finding implied that riboswitches are prevalent regulatory components in thermophiles. Riboswitches in organisms classified as hyperthermophiles were also identified (i.e., *Caldicellulosiruptor bescii*) that grow optimally at 75° C. Without being bound by theory, this suggests that riboswitches can fold into their functional conformations at temperatures at or above 75° C. The bioinformatics analyses did not encompass all riboswitch classes known to-date but only those we could obtain a co-variance model in the Rfam database. Riboswitch classes like the tungsten, nickel, and fluoride riboswitches were not included in the analyses disclosed herein. Thus, riboswitches play a regulatory role in the metabolic pathways of thermophilic bacteria.

In an embodiment, among the riboswitches discovered in thermophiles herein are purine riboswitches which are good candidates of synthetic regulators for gene expression. Their structural elements have been characterized extensively allowing for the rational design of their sequences for altered functionalities. These riboswitches bind to either guanine or adenine that can be added to the culture media at relatively high concentrations without toxicity to the host cell. Without being limited by theory, in the purine riboswitch class only a one nucleotide difference in the binding pockets may dictate whether the riboswitch binds guanine or adenine.

In non-thermophilic organisms, purine riboswitches have previously been used in synthetic biology due to their small size and modularity between the aptamer and the expression platform. As disclosed herein, only guanine-sensing purine riboswitches were found among the thermophilic genomes analyzed. Without being bound by theory, this suggested that thermophiles might have developed an alternative mode of adenine regulation.

As disclosed herein, natural purine riboswitches found in thermophiles were investigated for applications using two guanine-binding riboswitch sequences present in the genome of *Thermoanaerobacterium saccharolyticum* (T.s.) which is a thermophilic (optimal growth at 60° C.) and anaerobic bacterium. The two purine riboswitches in T.s. are located upstream of the genes encoding for xanthine permease (Tsac 2584 (SEQ ID NO: 1)) and inosine-5'-monophosphate dehydrogenases (Tsac 2588 (SEQ ID NO: 2)), which strongly suggests their regulatory roles in purine metabolism. The secondary structures of these RNAs were determined using the Mfold web server and indicate that these sequences adopt the canonical structure of purine riboswitches. In an embodiment, the secondary structures of these RNAs is depicted in FIGS. 10a and 10b.

To evaluate the T.s. riboswitches' regulatory activities, a thermophilic fluorescence reporter assay was used that included the use of super-folder green fluorescence protein (sfGFP) which is active in the aerobic thermophile, *Geobacillus thermoglucosidasius* (G.t.), at a growth temperature of 55° C. Both purine riboswitches from T.s. were inserted downstream of the pRp1S strong promoter respectively in plasmid pG1AK-sf such that the riboswitch controlled the expression of sfGFP once it was introduced into G.t. (see FIG. 2a and Table 1).

TABLE 1

Riboswitch construct sequences.

| Tsac 2584 riboswitch Construct (G.t) | AACAATCGTTAAAGCGGACGTTTTTGCGCCGCCCGGAT TTGCTTGAAAACTACCCGCTGACAGAAAAGCAAAAACG ATGGATCGAAGAGTGGAAAAAAGAAAAACAGTAGCTAT | Promoter (G.t -pRp1S) Riboswitch |
|---|---|---|
| | TGCGCATGATACAAGTTTATGCTACTATATTCCTTGTC AACTTAAGCGATTTGCTTAAGCGAGGAAAACGATGTTC CGCTGCAATGATGAAAAAGCATTG | RBS ATG-sfGFP |
| | ATTGTGTCAGGACAAGTAAATAATAGCTCATATAAT | |
| | TCTGAGAATACGGCTCAGAAGTCTCTACCAGACAA | |
| | CCGTAAATTGTCTGACTATGAGTGAAAGTGTACCTG | |

TABLE 1-continued

Riboswitch construct sequences.

| | | |
|---|---|---|
| | AGGGTTCCAGCCTTATTGTCCATGTGTAGAAAACAG | |
| | TAAAGGCGTTCGGACCGAGCGGTACAGGCATTGTA | |
| | TTGCCACACCTGTGGGATAAAAGCCCGGGAGGATA | |
| | GGTTTCACTCTATGTGTTGGAATCTATCATTCCGGG | |
| | CTTGTTTATTTTTAAAATTCGTTTTTATTT*TCTAGATA* | |
| | *AGGAGTGATTCGA*ATG | |
| Tsac 2588 riboswitch Construct (G.t) | *AACAATCGTTAAAGCGGACGTTTTTGCGCCGCCCGGAT TTGCTTGAAAACTACCCGCTGACAGAAAAGCAAAAACG ATGGATCGAAGAGTGGAAAAAAGAAAAACAGTAGCTAT* | Promoter (G.t -pRp1S) Riboswitch |
| | *TGCGCATGATACAAGTTTATGCTACTATATTCCTTGTGC AACTTAAGCGATTTGCTTAAGCGAGGAAAACGATGTTC CGCTGCAATGATGAAAAAGCATTG* | RBS ATG-sfG |
| | ATTGTGTCAGGACAAGTAAATAATAGCTCATATAAT | |
| | TCTGAGAATACGGCTCAGAAGTCTCTACCAGACAA | |
| | CCGTAAATTGTCTGACTATGAGTGAAAGTGTACCTG | |
| | AGGGTTCCAGCCTTATTGTCCATGTGTAGAAAACAG | |
| | TAAAGGCGTTCGGACCGAGCGGTACAGGCATTGTA | |
| | TTGCCACACCTGTGGGATAAAAGCCCGGGAGGATA | |
| | GGTTTCACTCTATGTGTTGGAATCTATCATTCCGGG | |
| | CTTGTTTATTTTTAAAATTCGTTTTTATTT*TCTAGATA* | |
| | *AGGAGTGATTCGA*ATG | |
| Tsac 2584 (non-binding) riboswitch Construct (G.t) | *AACAATCGTTAAAGCGGACGTTTTTGCGCCGCCCGGAT TTGCTTGAAAACTACCCGCTGACAGAAAAGCAAAAACG ATGGATCGAAGAGTGGAAAAAAGAAAAACAGTAGCTAT* | Promoter (G.t -pRp1S) Riboswitch |
| | *TGCGCATGATACAAGTTTATGCTACTATATTCCTTGTGC AACTTAAGCGATTTGCTTAAGCGAGGAAAACGATGTTC CGCTGCAATGATGAAAAAGCATTGAT*TGTGTCAGGAC | C to U binding mutant |
| | AAGTAAATAATAGCTCATATAATTCTGAGAATACG | RBS |
| | GCTCAGAAGTCTCTACCAGACAACCGTAAATTGTCT | ATG-sfG |
| | GATTATGAGTGAAAGTGTACCTGAGGGTTCCAGCC | |
| | TTATTGTCCATGTGTAGAAAACAGTAAAGGCGTTCG | |
| | GACCGAGCGGTACAGGCATTGTATTGCCACACCTGT | |
| | GGGATAAAAGCCCGGGAGGATAGGTTTCACTCTAT | |
| | GTGTTGGAATCTATCATTCCGGGCTTGTTTATTTTTA | |
| | AAATTCGTTTTTATTT*TCTAGATAAGGAGTGATTCGA*A | |
| | TG | |
| pbue (wt) riboswitch Construct (G.t) | *AACAATCGTTAAAGCGGACGTTTTTGCGCCGCCCGGAT TTGCTTGAAAACTACCCGCTGACAGAAAAGCAAAAACG ATGGATCGAAGAGTGGAAAAAAGAAAAACAGTAGCTAT* | Promoter (G.t -pRp1S) Riboswitch |
| | *TGCGCATGATACAAGTTTATGCTACTATATTCCTTGTGC AACTTAAGCGATTTGCTTAAGCGAGGAAAACGATGTTC CGCTGCAATGATGAAAAAGCATTG* | RBS ATG-sfGFP |
| | GGAAACGAATCAATTAAATAGCTATTATCACTTGTA | |
| | TAACCTCAATAATATGGTTTGAGGGTGTCTACCAGG | |
| | AACCGTAAAATCCTGATTACAAAATTTGTTTATGAC | |
| | ATTTTTTGTAATCAGGATTTTTTTATTTATCAAAAC | |
| | ATTTAAGTAAA*TCTAGATAAGGAGTGATTCGA*ATG | |

TABLE 1-continued

Riboswitch construct sequences.

| | | |
|---|---|---|
| pbue (P1 = 8) riboswitch Construct (G.t) | *AACAATCGTTAAAGCGGACGTTTTTGCGCCGCCCGGAT*<br>*TTGCTTGAAAACTACCCGCTGACAGAAAAGCAAAAACG*<br>*ATGGATCGAAGAGTGGAAAAAAGAAAAACAGTAGCTAT*<br>*TGCGCATGATACAAGTTTATGCTACTATATTCCTTGTGC*<br>*AACTTAAGCGATTTGCTTAAGCGAGGAAAAACGATGTTC*<br>*CGCTGCAATGATGAAAAAGCATTG*<br><u>GGAAACGAATCAATTAAATAGCTATTATATTTTGTA</u><br><u>TAACCTCAATAATATGGTTTGAGGGTGTCTACCAGG</u><br><u>AACCGTAAAATCCTGATTACAAAATTTGTTTATGAC</u><br><u>ATTTTTTGTAATCAGGATTTTTTTATTTATCAAAAC</u><br><u>ATTTAAGTAAA*TCTAGATAAGGAGTGATTCGA*ATG | Promoter (G.t -pRp1S) Riboswitch mutation RBS ATG-sfG |
| pbue (P1 = 10) riboswitch Construct (G.t) | *AACAATCGTTAAACGCGGACGTTTTTGCGCCGCCCGGAT*<br>*TTGCTTGAAAACTACCCGCTGACAGAAAAGCAAAAACG*<br>*ATGGATCGAAGAGTGGAAAAAAGAAAAACAGTAGCTAT*<br>*TGCGCATGATACAAGTTTATGCTACTATATTCCTTGTGC*<br>*AACTTAAGCGATTTGCTTAAGCGAGGAAAAACGATGTTC*<br>*CGCTGCAATGATGAAAAAGCATTG*<br><u>GGAAACGAATCAATTAAATAGCTATTAAATTTTGT</u><br><u>ATAACCTCAATAATATGGTTTGAGGGTGTCTACCAG</u><br><u>GAACCGTAAAATCCTGATTACAAAATTTGTTTATGA</u><br><u>CATTTTTTGTAATCAGGATTTTTTTATTTATCAAAA</u><br><u>CATTTAAGTAAATCTAGATAAGGAGTGATTCGAATG | Promoter (G.t -pRp1S) Riboswitch mutation RBS ATG-sfG |
| adhe constitutive expression (C.t) | *GATAAACAAAGGACGGTTCAGGGCTTCTGCTCATCC*<br>*TACTCTGCATTGTAAAAAGGTAGGATGAATTTTTATTT*<br>*TTAATCTTATTGAAAAAAATTTTTGAAAATCGGTTTTAT*<br>*TAAAAAAAAGTGGGTATATTTATAATAGTCAATTGATT*<br>*GGTTAAAAAAATTTAAATAAGCAAACAGAATAATAACA*<br>*AAGTAAGGAGGAATTTGTTATG | Promoter (Clo1515_2365) ATG-adhE |
| Adhe pbuE (wt) (C.t.) | *GATAAACAAAGGACGGTTCAGGGCTTCTGCTCATCC*<br>*TACTCTGCATTGTAAAAAGGTAGGATGAATTTTTATTT*<br>*TTAATCTTATTGAAAAAAATTTTTGAAAATCGGTTTTAT*<br>*TAAAAAAAAGTGGGTATATTTATAATAGTCAATTGATT*<br>*GGTTAAAAAAATTTAAATAAGCAAACAGAATAATAAG*<br><u>GAAACGAATCAATTAAATAGCTATTATCACTTGT</u><br><u>ATAACCTCAATAATATGGTTTGAGGGTGTCTACC</u><br><u>AGGAACCGTAAAATCCTGATTACAAAATTTGTTT</u><br><u>ATGACATTTTTTGTAATCAGGATTTTTTTATTTA</u><br><u>TCAAAACATTTAAGTAAAAAAAGTAAGGAGGAATT</u><br><u>TGTTATG | Promoter (Clo1515_2365) Riboswitch ATG-adhE |
| pbue (P1 = 8) riboswitch Construct (C.t) | *GATAAACAAAGGACGGTTCAGGGCTTCTGCTCATCC*<br>*TACTCTGCATTGTAAAAAGGTAGGATGAATTTTTATTT*<br>*TTAATCTTATTGAAAAAAATTTTTGAAAATCGGTTTTAT*<br>*TAAAAAAAAGTGGGTATATTTATAATAGTCAATTGATT*<br>*GGTTAAAAAAATTTAAATAAGCAAACAGAATAATAAG*<br><u>GAAACGAATCAATTAAATAGCTATTATATTTTGT</u><br><u>ATAACCTCAATAATATGGTTTGAGGGTGTCTACC</u><br><u>AGGAACCGTAAAATCCTGATTACAAAATTTGTTT</u><br><u>ATGACATTTTTTGTAATCAGGATTTTTTTATTTA</u><br><u>TCAAAACATTTAAGTAAAAAAAGTAAGGAGGAATT</u><br><u>TGTTATG | Promoter (G.t -pRp1S) Riboswitch mutation RBS ATG-sfG |

Figure 8:
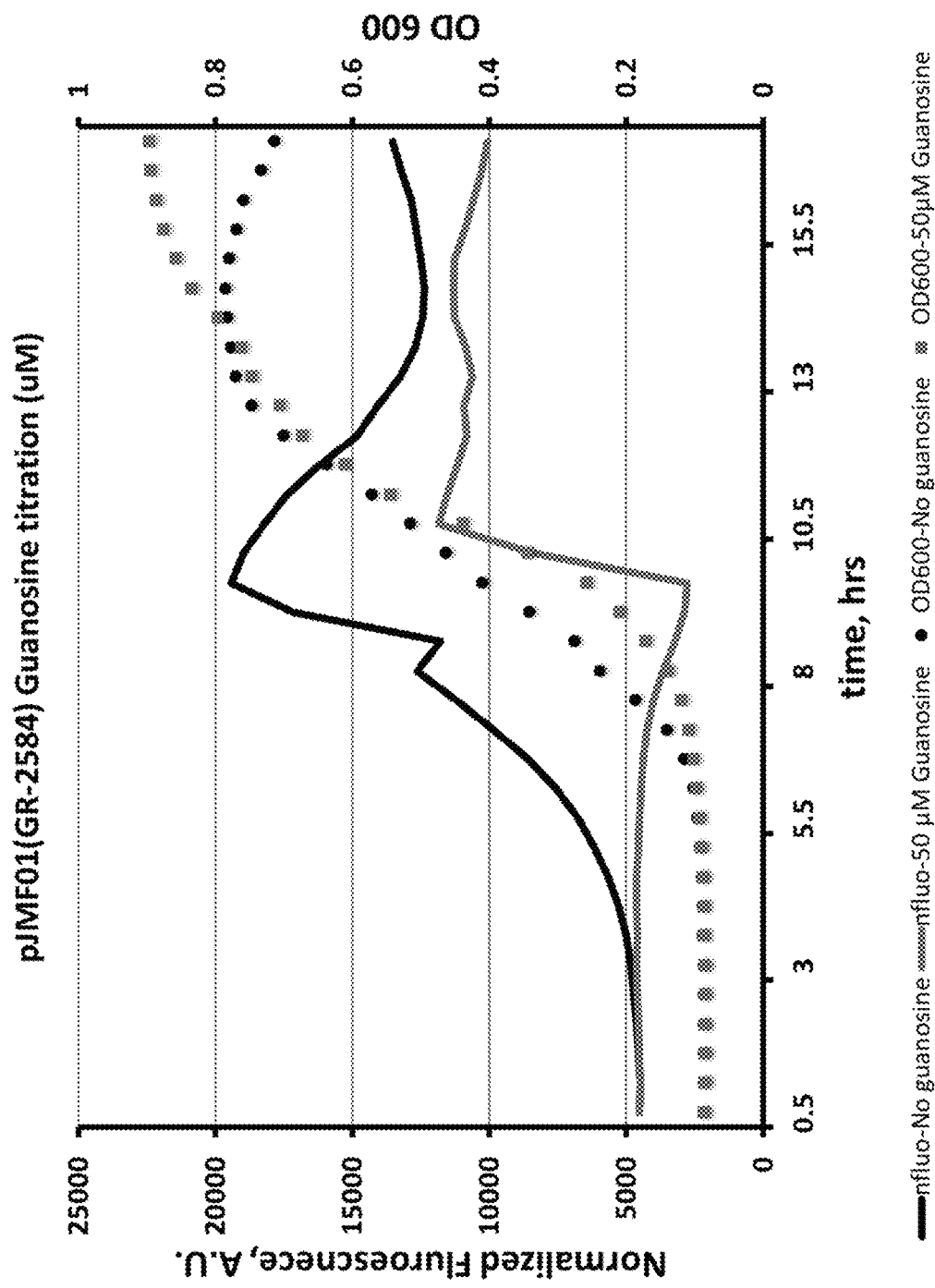
FIG. 8 depicts the normalized fluorescence in cell cultures expressing a super-folder GFP.

It was observed that the G. t. cultures achieved a maximal normalized fluorescence at the mid-exponential growth stage, and it was this growth phase that was used to compare the riboswitch regulatory effect at different ligand concentrations (see FIG. 8). To trigger the regulatory response from the riboswitches, guanosine was used as the ligand as cells can import the compound and convert it into guanine enzymatically. As disclosed herein, when 0.25 mM of guanosine was added, the maximal normalized fluorescence was reduced from 38±1 to 15±0.1 fluorescence units (about a 2.5-fold change) in the cultures carrying the Tsac 2588 riboswitch and from 20±2 to 2.8±0.1 (about a 7-fold change) for the cultures carrying the Tsac 2584 riboswitch (see FIG. 2c). No repression was observed for cells carrying the parental pG1AK plasmid which constitutively expresses sfGFP in the absence of a riboswitch. As an additional control, a point mutation was introduced in the Tsac 2584 aptamer domain at position 74 (C74U). Position 74 is responsible for its interaction with guanine. With this mutation, the guanosine-dependent repression seen in the wild-type sequences was no longer observed (see FIG. 9).

For the 2584 riboswitch, the fluorescence level approaches the background autofluorescence which is indicative of a tight repression, while the 2588 riboswitch displays about 30% of fluorescence in comparison to the control pG1AK parental plasmid. The insertion of either riboswitch into the system causes a basal reduction in gene expression without adding guanosine.

Thus, in an embodiment, these results represent the first in-vivo characterization of riboswitch sequences in thermophilic bacteria. The regulatory mode of the T.s. riboswitches was experimentally determined to be repression rather than activation, and the reporter system enabled the measurements of riboswitch activity at 55° C. The two T.s. riboswitches demonstrated gene repression to different extents and ranges.

While the ability to tune down gene expression is valuable for research and biotechnological applications, riboswitches can also serve as inducers of gene expression upon binding a ligand. To establish an inducible system for thermophiles, riboswitch sequences from a mesophilic organism were used to upregulate gene expression in a thermophile. The pbuE riboswitch (SEQ ID NO: 3) from *Bacillus subtilis* is an adenine-binding riboswitch that has been used as a biochemical and biophysical model for RNA structure-to-function relationships. This riboswitch is a strong transcriptional terminator in its expression platform and is capable of achieving a tight transcriptional control of a downstream gene. When the ligand binds the aptamer, the aptamer conformation is favored, which prevents the terminator from interfering with the polymerase, thereby allowing transcription of the downstream gene(s).

Figures 3A, 3B:
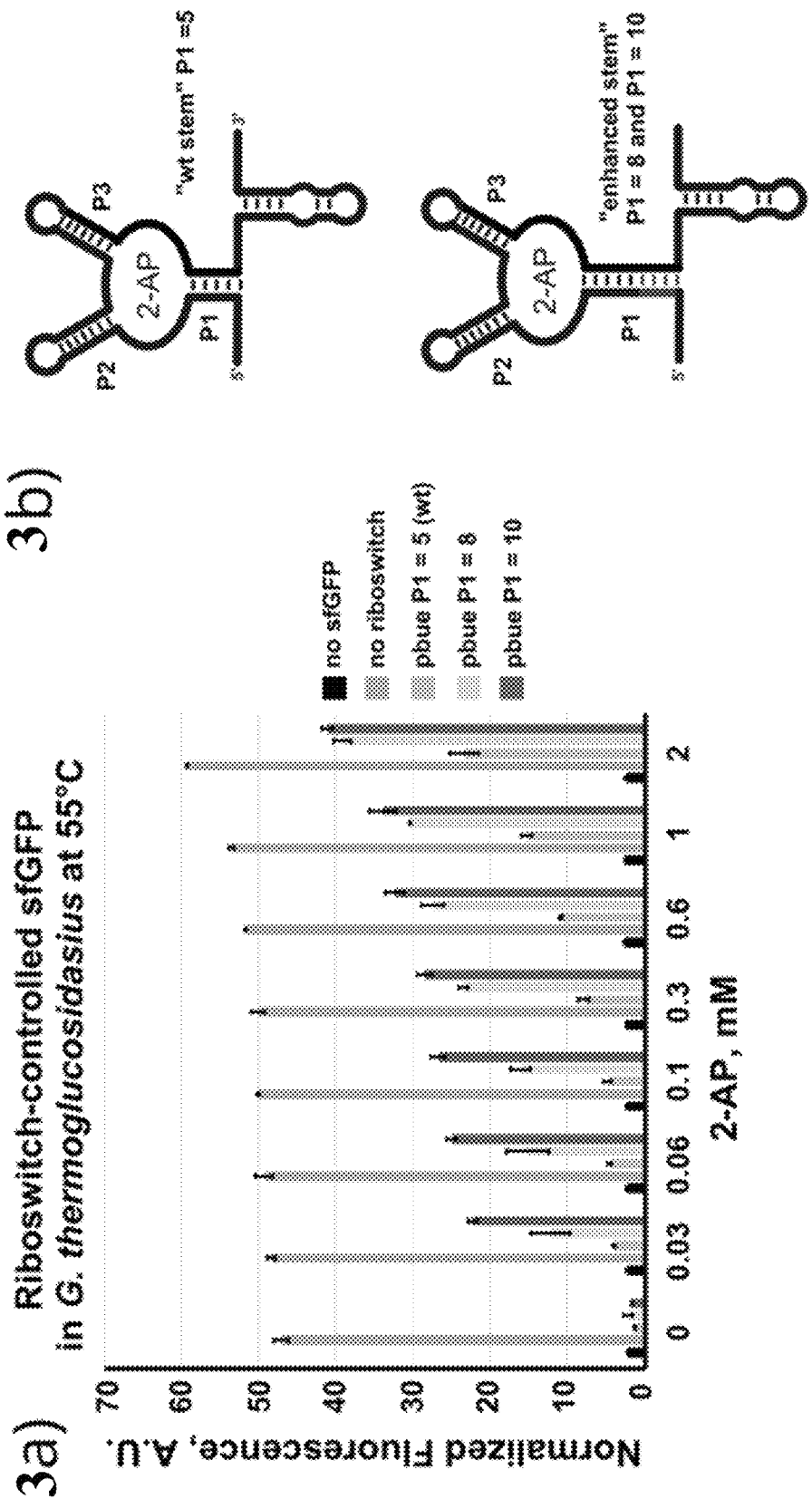
FIG. 3a depicts 2-aminopurine (2-AP)-dependent induction of gene expression mediated by a mesophilic pbuE riboswitch tested in *G. thermoglucosidasius* at 55° C.
FIG. 3b depicts the secondary structures without and with mutations elongating P1 that stabilizes the aptamer domain.

Similar to the scheme depicted in FIG. 2a, pbuE riboswitch was introduced into a construct and the regulatory response was quantified with normalized fluorescence in increasing concentrations of 2-aminopurine (2-AP) in G.t. using sfGFP at 55° C. (see FIG. 3a). 2-AP as a ligand has been shown to elicit a response from pbuE riboswitch both in-vitro and in-vivo at 37° C. In the absence of 2-AP, all constructs containing a pbuE-derived riboswitch displayed a fluorescence level similar to the background from cells not expressing sfGFP, demonstrating a tight transcriptional repression from the riboswitch's terminator. When 2 mM of 2-AP was added to the culture, the normalized fluorescence increased from 1.4±0.02 to 23±1.8 (about a 16-fold change) which accounts for about 40% of the fluorescence observed for the culture constitutively expressing sfGFP (59±8.9) without a riboswitch. While this riboswitch is responsive to 2-AP in upregulating the gene expression in G.t., a relatively high dose of 2-AP was required to elicit the regulatory response. To increase the sensitivity and dynamic range of the inducible system, rational mutations were introduced in the 5' side of the P1 paired region to elongate P1 from 5 base pairs (wt) to 8 and 10 base pairs which favored the aptamer domain over the terminator (see FIG. 3b). Thus, it was determined that at 2 mM 2-AP, riboswitches with elongated P1 resulted in an increased maximal normalized fluorescence of 39.1±1.1 (about a 24-fold change) and 41.1±0.6 (about a 29-fold change) for P1=8 bp (SEQ ID NO: 4) and P1=10 bp (SEQ ID NO: 5), respectively. The fluorescence becomes about 80% of that observed by the constitutive promoter lacking a riboswitch, and the mutated riboswitches displayed an increased regulatory range by about 22% over the wild-type riboswitch at 2 mM 2-AP. Moreover, the riboswitch mutant (P1=10 bp) was activated up to 50% of the expression, as compared to the no riboswitch control, at a concentration of 300 µM which indicates improved sensitivity to 2-AP over the wild type sequence. Thus, in an embodiment, these results demonstrate that the range of expression to which a riboswitch can regulate and its sensitivity to the ligand can be increased with rational engineering of their secondary structure.

Beyond characterizing and demonstrating the activity of riboswitches activities in *G. thermoglucosidasius* with a reporter protein, riboswitches that can be applied to tuning the expression of a gene important in a functional pathway in vivo was investigated. In an embodiment, the riboswitch in a thermophilic and anaerobic bacterium, *Clostridium thermocellum* (C.t.) was investigated. C.t. has previously been used in biotechnological applications which rely upon an expensive laminaribiose-inducible promoter system. In an embodiment, ethanol production by C.t. was used as an indicator of the riboswitch activity.

Ethanol production in C.t. relies primarily on the NADH-dependent bifunctional alcohol and aldehyde dehydrogenase encoding gene, adhE (clo1313_1798). The deletion of the adhE gene in C.t. reduced ethanol production by greater than 95%.

Figure 7:
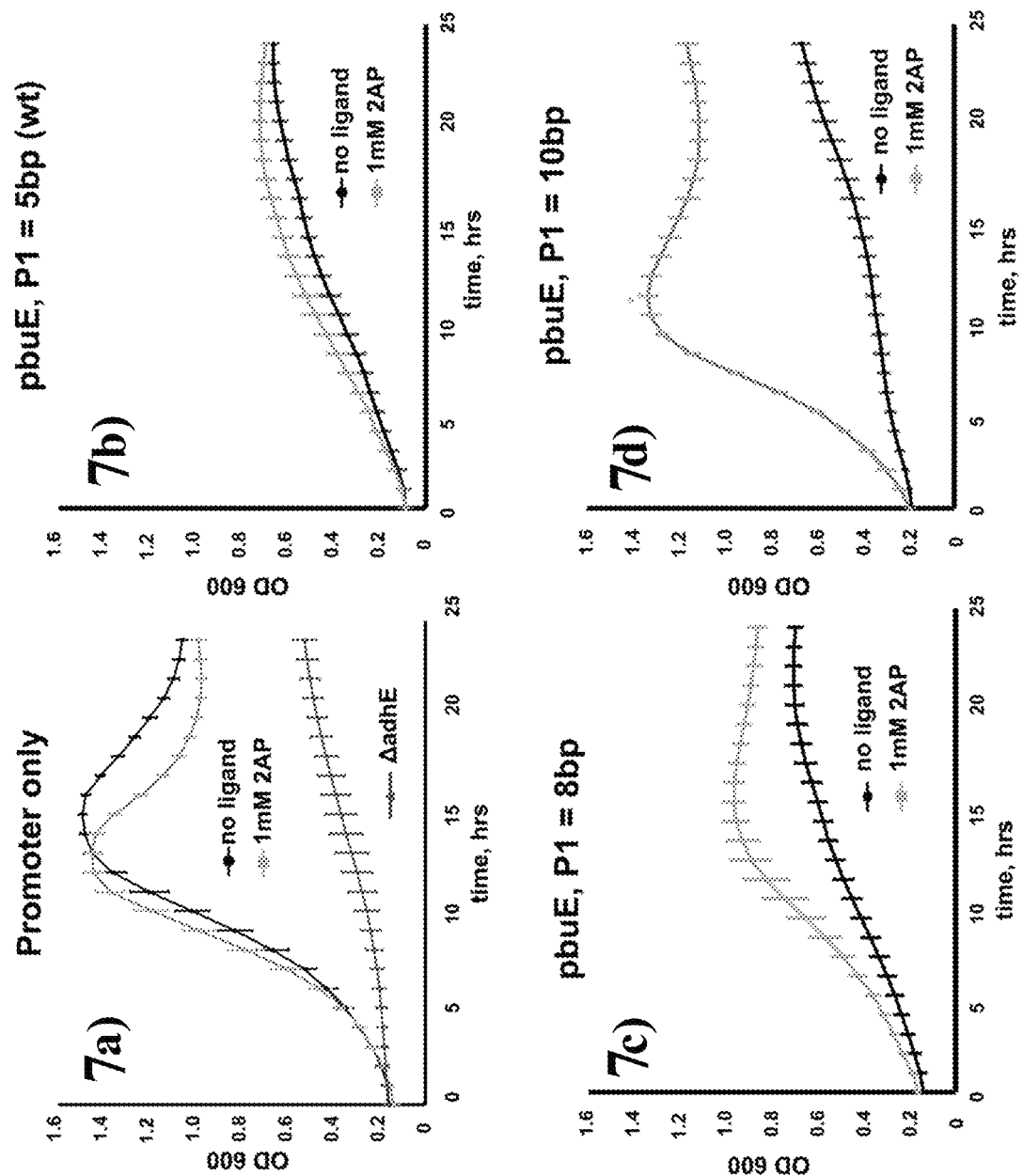
FIG. 7a depicts the growth profile for the plasmid-based complementation of adhE gene under the control of pbuE riboswitch with the promoter only.
FIG. 7b depicts the growth profile for the plasmid-based complementation of adhE gene under the control of pbuE riboswitch with the wild-type aptamer of the pbuE riboswitch.
FIG. 7c depicts the growth profile for the plasmid-based complementation of adhE gene under the control of pbuE riboswitch with the 8 bp aptamer of the pbuE riboswitch.
FIG. 7d depicts the growth profile for the plasmid-based complementation of adhE gene under the control of pbuE riboswitch with the 10 bp aptamer of the pbuE riboswitch.

The production of ethanol provides an important NADH sink for the bacteria and adhE is one of the most highly expressed genes in C.t. Deleting the chromosomal copy of adhE resulted in a strain with impaired growth in rich media (max $OD_{600}$ of about 0.4, see FIG. 7a). To assess the effect of riboswitch activity on ethanol production, growth, and other major fermentation products in the 2-AP induced versus uninduced states, adhE gene was transcriptionally fused to the clo1313_2638 promoter native to C.t. and expressed from a plasmid pJMK06 (see FIG. 5) in the ΔadhE mutant at 55° C. In the adhE complementation strain, growth was restored to the wild-type level (max $OD_{600}$ of about 1.4, see FIG. 7a). Fermentation products, ethanol, lactic acid, and acetic acid quantified 40 hours post inoculation were normalized by the sugar consumed. Without a riboswitch, ethanol accounted for 55% of the fermentation products while lactic acid accounted for 15% (see FIG. 4) in the adhE complementation strain. This product distribution was similar to that of the wild-type strain (about 55% ethanol and 20% lactic acid, see Table 2).

TABLE 2

Plasmids

| Plasmid name | Promoter | Riboswitch | Reporter | Mode of regulation | Ligand | Host for assay |
|---|---|---|---|---|---|---|
| pJMF01 | pRp1S | Tsac 2584 (SEQ ID NO: 1) | sfGFP | "off" | guanosine | G.t. |
| pJMF02 | pRp1S | Tsac 2584 | sfGFP | *mutant | guanosine | G.t. |
| pJMF03 | pRp1S | Tsac 2588 (SEQ ID NO: 2) | sfGFP | "off" | guanosine | G.t. |
| pJMF10 | pRp1S | pbuE-wt (SEQ ID NO: 3) | sfGFP | "on" | 2-AP | G.t. |
| pJMF11 | pRp1S | pbuE-P1 = 8 bp (SEQ ID NO: 4) | sfGFP | "on" | 2-AP | G.t. |
| pJMF12 | pRp1S | pbuE-P1 = 10 bp (SEQ ID NO: 5) | sfGFP | "on" | 2-AP | G.t. |
| pJMK06 | Clo1313_2638 | No riboswitch | C.t. adhE | N.A. | 2-AP | C.t. |
| pJMK09 | Clo1313_2638 | pbuE-wt | C.t. adhE | "on" | 2-AP | C.t. |
| pJMK11 | Clo1313_2638 | pbuE-P1 = 8 bp | C.t. adhE | "on" | 2-AP | C.t. |
| pJMK12 | Clo1313_2638 | pbuE-P1 = 10 bp | C.t. adhE | "on" | 2-AP | C.t. |

PbuE-derived riboswitches including the wild-type and the two elongated P1 riboswitches were introduced into the Clo1313_2638 promoter to drive the expression of adhE following the scheme depicted in FIG. 2b.

Figure 4:
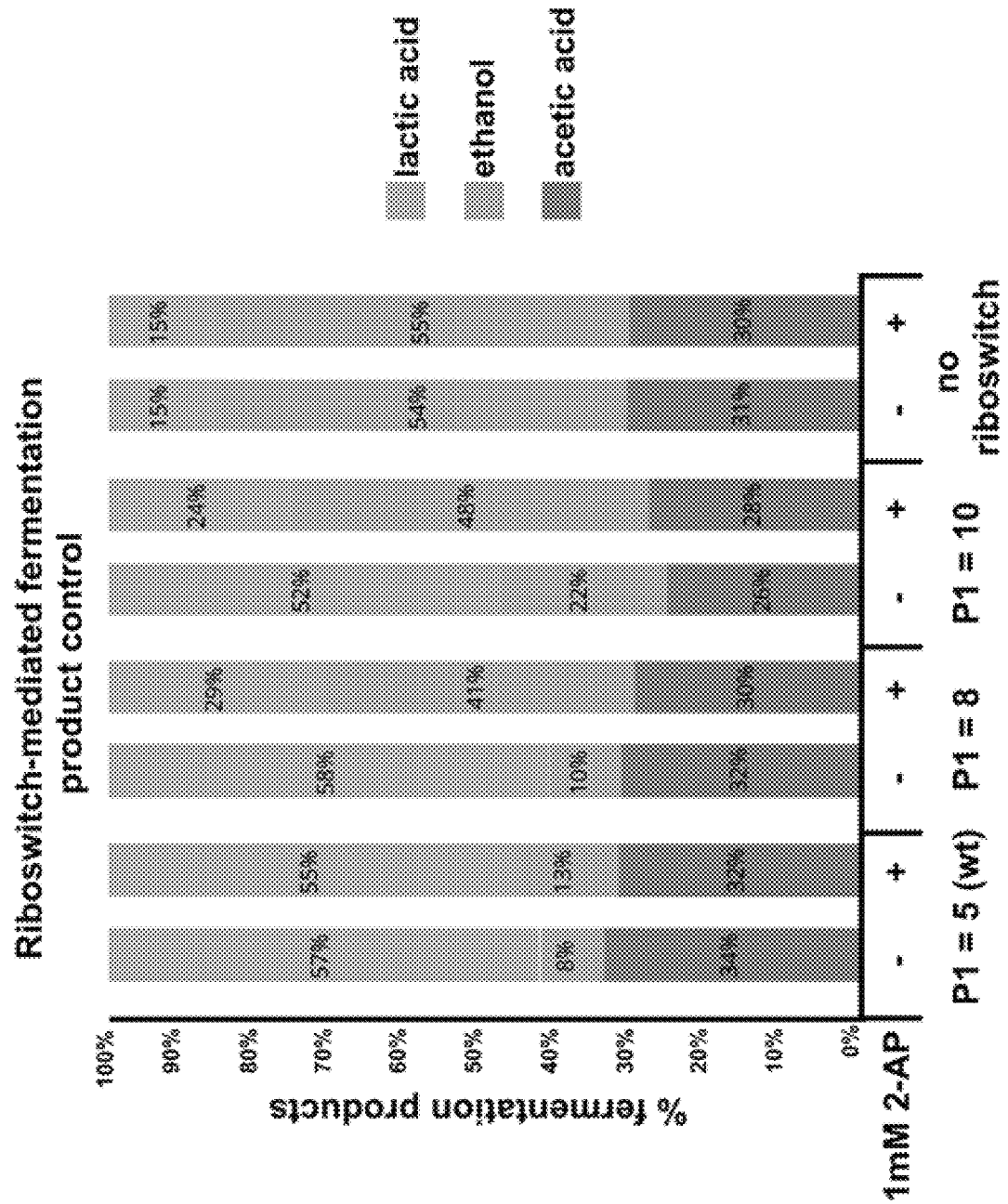
FIG. 4 depicts a fermentation product profile for the riboswitch-controlled expression of adhE gene in *C. thermocellum*. The fermentation products were quantified using HPLC and the percentages represent the average of three experiments.
Figure 5:
FIG. 5 depicts a plasmid map of pJMK06 plasmid. This plasmid was designed to replicate both in *E. coli* and *C. thermocellum*. A synthetic terminator insulates the expression of the adhE gene from the *C. thermocellum* gapDH promoter that drives the CAT gene from resistance to thiamphenicol.
Figure 6:
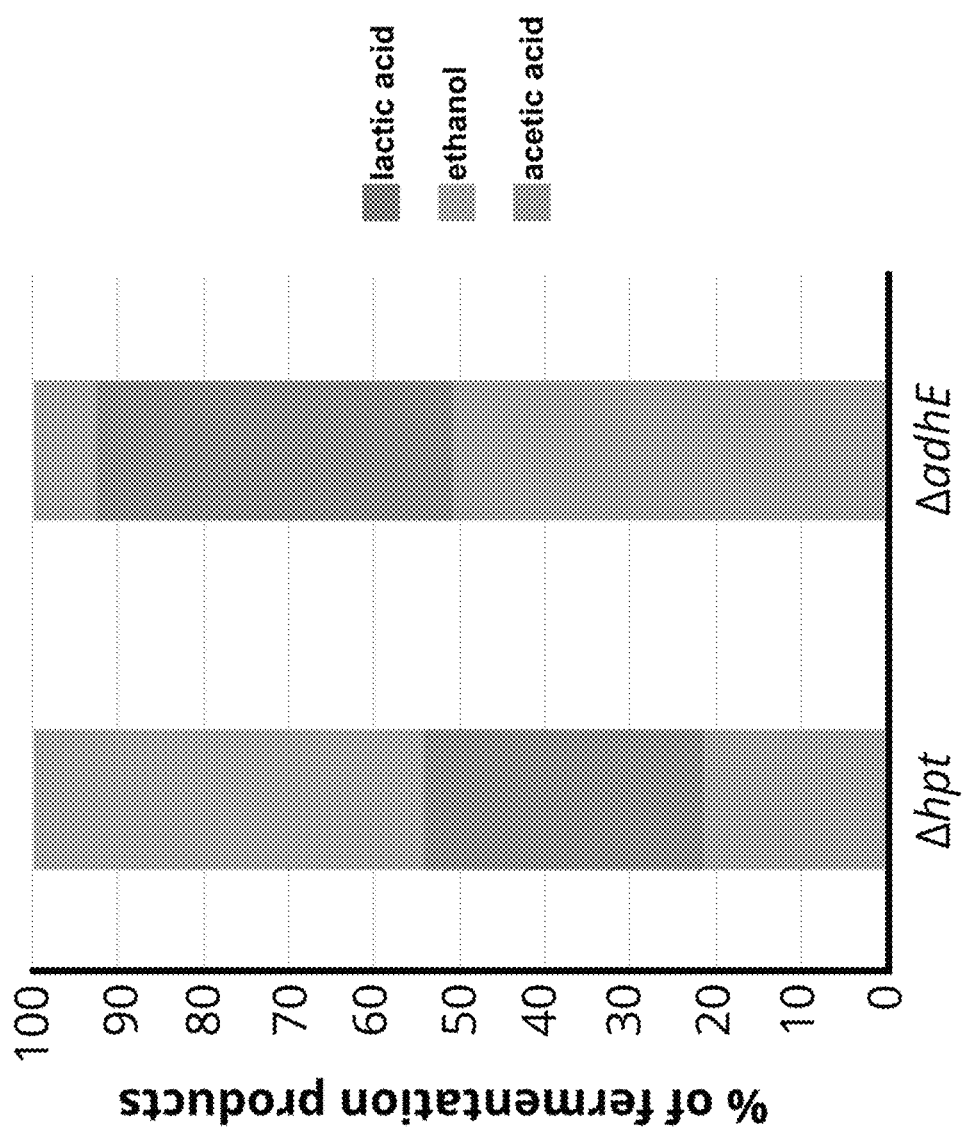
FIG. 6 depicts a fermentation profile of a *C. thermocellum* adhE deletion mutant.

In an embodiment, as depicted in FIG. 4, ethanol production ranged below 22% in all the uninduced conditions, and the cells generated 52-57% of lactic acid. When 2-AP was added to the culture to induce adhE expression, ethanol production remained unchanged in the culture without a riboswitch. However, for the cultures with P1=8 and P1=10 riboswitch variants, ethanol accounted for 41% and 48% of the fermentation output, respectively (see FIG. 4). As ethanol production increased in the 2-AP induced cultures, lactic acid production decreased. Without being bound by theory, since lactate production catalyzed by lactate dehydrogenase is also a NADH sink in *C. thermocellum*, its production may compensate for the removal of NADH sink when ethanol is not produced. This data demonstrated riboswitch-mediated induction of adhE gene expression and consequent re-direction of the metabolic flux between lactic acid and ethanol.

The growth response to riboswitch-mediated adhE expression in the adhE complementation strain was demonstrated with and without 2-AP. In the absence of 2-AP, the growth for the cultures expressing the adhE under the control of the riboswitches resembled that of the adhE mutant with no plasmid, indicating that the riboswitch was tightly repressing the adhE gene (see FIGS. 7b-d). When 1 mM 2-AP was added to the media, no substantial improvement in growth was observed for the culture carrying the wild-type riboswitch plasmid (see FIG. 7b), but growth improvement was observed in the cell culture carrying the pbuE P1 mutants (see FIGS. 7c-d). For the riboswitch mutant P1=10, the maximal $OD_{600}$ reached 0.6 without 2-AP but reached 1.4 with 1 mM 2-AP. The riboswitch activity resulted in a growth phenotype and restored the adhE expression, and appeared to improve the fitness of the bacteria. These results were consistent with the riboswitch activities observed in the *G. thermoglucosidasius* reporter assay in which higher levels of sfGFP at 1 mM of 2-AP was observed in the P1=10 mutant than that in wild-type (see FIG. 3a).

As disclosed in Table 3, the millimolar amounts of the fermentation products were quantified by HPLC. The numbers represent the average values of three independent experiments.

TABLE 3

Quantification of fermentation products of *C. thermocellum*

| construct | Lactic acid, mM | Acetic acid, mM | Ethanol, mM | Total products, mM |
|---|---|---|---|---|
| pbuE wt | 11.87 ± 1.22 | 7.09 ± 0.33 | 1.73 ± 0.16 | 20.68 ± 1.62 |
| pbuE wt + 2AP | 15.77 ± 0.51 | 9.35 ± 0.07 | 3.78 ± 0.06 | 28.90 ± 0.64 |
| pbuE (P1 = 8) | 14.08 ± 1.66 | 7.62 ± 0.68 | 2.38 ± 0.50 | 24.09 ± 2.72 |
| pbuE (P1 = 8) + 2AP | 10.64 ± 0.02 | 11.14 ± 0.57 | 15.61 ± 5.29 | 37.39 ± 5.81 |
| pbuE (P1 = 10) | 14.92 ± 0.78 | 7.50 ± 1.65 | 6.38 ± 1.41 | 28.80 ± 2.34 |
| pbuE (P1 = 10) + 2AP | 8.87 ± 0.44 | 10.14 ± 0.15 | 17.31 ± 0.44 | 36.32 ± 1.00 |
| no riboswitch | 2.18 ± 0.59 | 4.60 ± 1.34 | 8.20 ± 3.28 | 14.98 ± 5.21 |
| no riboswitch + 2AP | 2.13 ± 0.35 | 4.38 ± 0.95 | 8.02 ± 2.40 | 14.53 ± 3.71 |

| construct | Lactic acid % | Acetic acid % | Ethanol % |
|---|---|---|---|
| pbuE wt | 57 ± 2 | 34 ± 2 | 8 ± 1 |
| pbuE wt + 2AP | 55 ± 1 | 32 ± 1 | 13 ± 1 |
| pbuE (P1 = 8) | 58 ± 1 | 32 ± 1 | 10 ± 1 |
| pbuE (P1 = 8) + 2AP | 29 ± 4 | 30 ± 3 | 41 ± 7 |
| pbuE (P1 = 10) | 52 ± 6 | 26 ± 3 | 22 ± 3 |
| pbuE (P1 = 10) + 2AP | 24 ± 1 | 28 ± 1 | 48 ± 1 |

TABLE 3-continued

| Quantification of fermentation products of C. thermocellum | | | |
|---|---|---|---|
| no riboswitch | 15 ± 1 | 31 ± 2 | 54 ± 3 |
| no riboswitch + 2AP | 15 ± 1 | 30 ± 1 | 55 ± 3 |

In an embodiment, and as depicted in FIG. 8, the normalized fluorescence of the cell culture is defined as:

$$nfluo = \frac{\text{raw fluorescence of the culture}}{\text{optical density of the culture } (OD600)}$$

When the normalized fluorescence is plotted with the growth curve, it is observed that maximal normalized fluorescence occurs reproducibly at the mid-exponential growth phase, which is consistently the case across cell cultures with different final ligand concentrations. To compare the normalized fluorescence between cultures growing with different ligand concentrations, the normalized fluorescence for each culture was averaged between the mid-log points where the OD was between 0.4 and 0.6.

Figure 9:
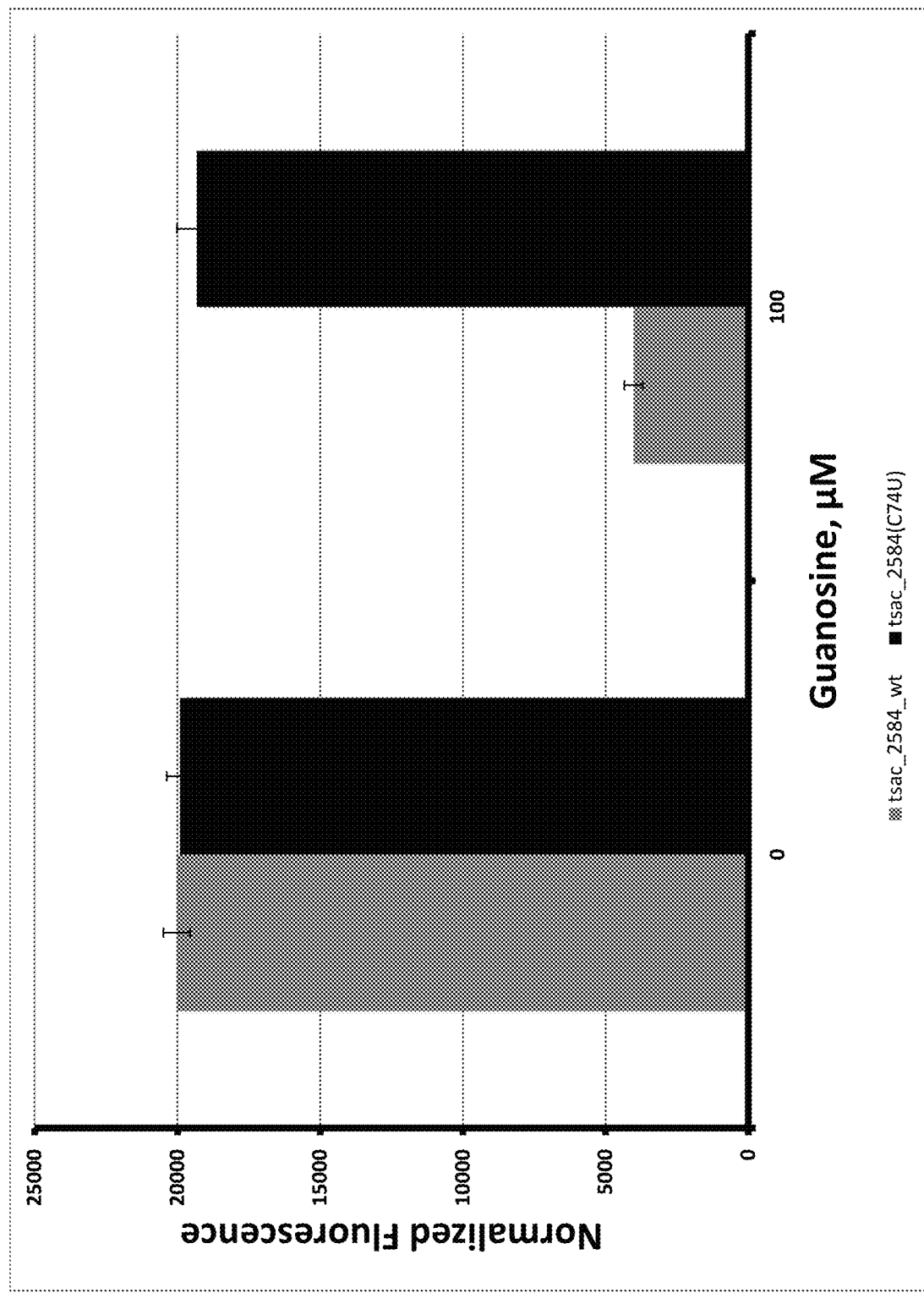
FIG. 9 depicts tsac 2584 non-binding mutant control.
Figure 11:
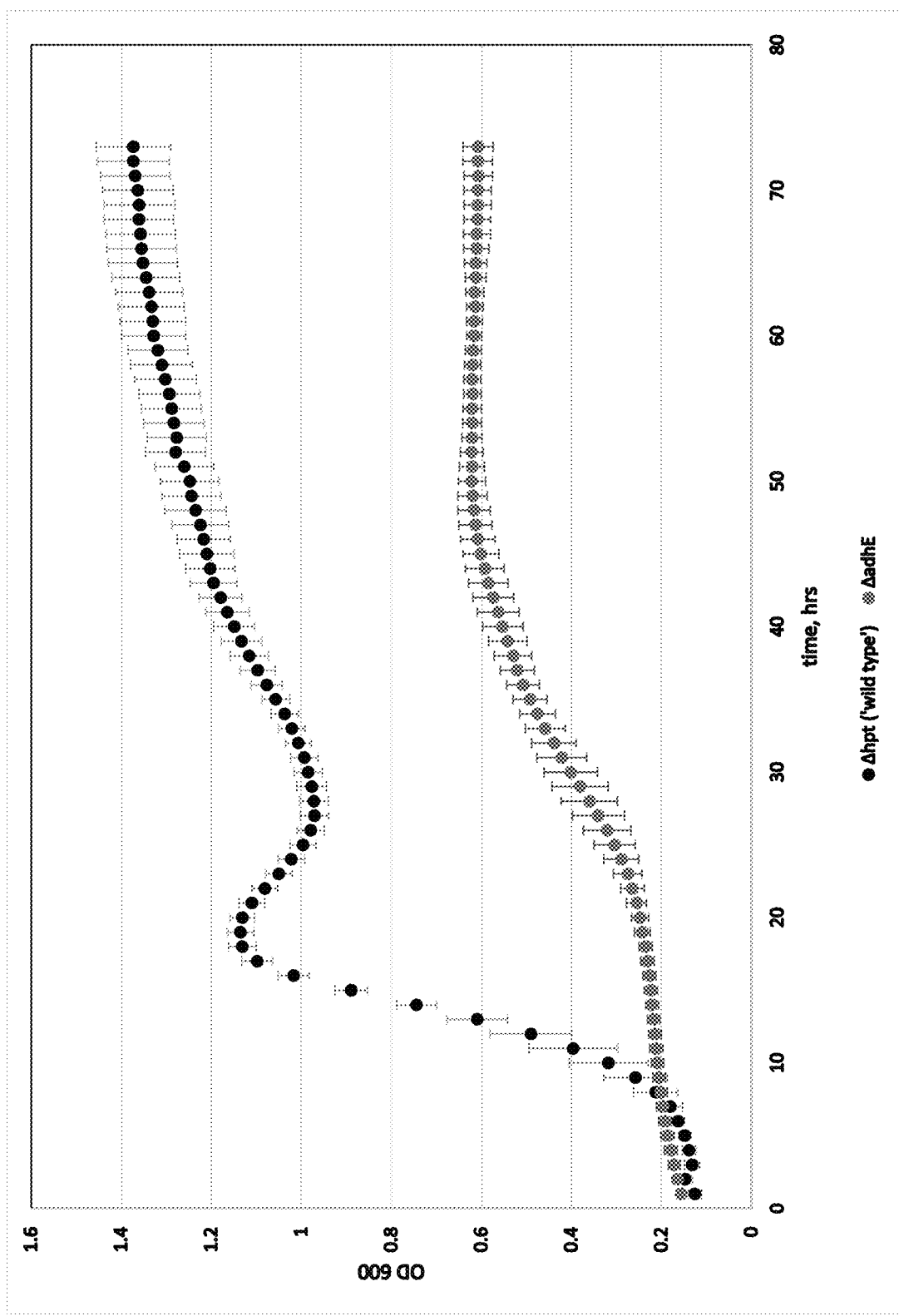
FIG. 11 depicts the growth comparison between Δhpt ("wild-type") and ΔadhE. To enable a genetically tractable strain of *Clostridium thermocellum* a deletion mutant to the hypoxanthine phosphoribosyl transferase (hpt) gene was created that allows for counter selection. This strain is designated as the "wild-type". This is the parental strain used to construct ΔadhE deletion that was used in the plasmid complementation experiments.

In an embodiment, as depicted in FIG. 9, the regulatory response observed from the *T. saccharolyticum* is due to guanosine-dependent riboswitch activity. A mutation was introduced in the aptamer of the 2584 riboswitch at the conserved position where guanine interacts with the RNA through a canonical Watson-Creek interaction (cytosine at position 74 to a uridine). This mutant no longer exhibited the regulatory response induced by the wild-type riboswitch.

*G. thermoglucosidasius* experiments were perform using the DSM 2542T strain (*Geobacillus* Genetic Stock Center, Colombus Ohio). Experiments in *C. thermocellum* were performed in a DSM 1313 (DSMZ, Brunswick Germany) derived strain with the hpt (clo1313_2927) gene deleted for counter-selection purposes 26 and Δhpt is referred to as the wild-type host strain. The two purine riboswitch sequences from *T. saccharolyticum* were amplified with PCR from the DSM 8691 strain (DSMZ, Brunswick Germany). The replicating plasmid pG1AK for *G. thermoglucosidasius* was a gift from Tom Ellis. Plasmid pJMK06 was constructed for gene expression in *C. thermocellum*. PCR and cloning was performed using Q5 High fidelity polymerase and Hi-Fi DNA assembly master mix, respectively (New England Biolabs, MA). Both *C. thermocellum* and *G. thermoglucosidasius* were transformed by electroporation following previous published protocols. The resulting *G. thermoglucosidasius* transformants were cultivated in a defined glucose medium (DG) while the fluorescence of the culture was tracked. The adhE gene was deleted in a *C. thermocellum* background strain with an altered hydrogenase (clo1313_1791) gene expression to presumably compensate for the redox imbalance created by the lack of ethanol formation.

Identification of riboswitches in thermophilic bacteria: The genome sequences of the thermophilic bacteria were obtained from the RefSeq database and analyzed for the presence of riboswitches using the INFERNAL software package.

Riboswitch Activity Assays in *G. thermoglucosidasius*:

*G. thermoglucosidasius* strains transformed with different plasmids were grown aerobically overnight in 5 ml TGP media (supplemental) with 12.5 μg/mL kanamycin at 55° C. and shaken at 200 rpm. The freshly grown overnight culture was used to inoculate 5 mL of fresh TGP media with kanamycin and incubated in the same condition for about 5 hrs when the cultures reached $OD_{600}$ of about 1.0. This secondary growth culture was used to inoculate 5 ml of Defined Glucose Media (DG) with 250-fold dilution and was sub-aliquoted into a 96-well plate with 200 microliters per well where different concentrations of the effector ligand was added. The plate was incubated in a Greiner-Bio xxx plate reader and the $OD_{600}$ and the fluorescence intensity (details of excitation and emission) was tracked for 24 hrs. To quantify the normalized fluorescence, the value of the raw fluorescence was taken when the cells were in mid-exponential phase ($OD_{600}$ 0.4-0.6) and divided by the optical density to normalize the fluorescence.

*C. thermocellum* Growth:

*C. thermocellum* strains were grown at 55° C. and shaken at 100 rpm in sealed "Balch type" tubes containing 10 mL CTFUD rich media and 0.5% (w/v) cellobiose as the main carbon source. Strains expressing adhE with and without a pbuE riboswitch upstream were initially cultured in tubes until mid-log phase ($OD_{600}$ of about 0.3-0.4) and then diluted to an $OD_{600}$ at about 0.1. To measure cell growth, the diluted culture was sub-aliquoted into a 96-well plate where 2-aminopurine (2-AP) was added to the concentrations indicated in the experiment in triplicates. Cell growth was continuously measured in Greiner-Bio 96-well plates incubated anaerobically in a BioTek plate reader. To measure *C. thermocellum* fermentation products in strains carrying the respective plasmids expressing the adhE gene under the control of pbuE riboswitch and mutated riboswitches, cells were grown in 10 mL CTFUD rich media containing 0.5% (w/v) cellobiose. After 40 hours of incubation, 1 mL of the culture was centrifuged and the supernatant was filtered through a 0.22 μM membrane. Fermentation products including ethanol, acetate, and lactate were measured by HPLC (1200 series; Agilent Technologies, Santa Clara, Calif.) with a mobile phase of 4 mM sulfuric acid (flow rate of 0.6 ml/min) using an Aminex HPX-87H column with a Micro Guard Cation H Cartridge. The column temperature was set to 55° C.

*C. thermocellum* Growth Media and Strain Development:

The C.t. culturing media, CTFUD, was made following a protocol published previously. The adhE gene was targeted deleted in a host strain in which the entire non-coding region containing the promoter of the clo1313_2638 gene was inserted immediately upstream of the gene encoding for the evolving hydrogenase catalytic subunit (clo1313_1791) in the genome. The altered hydrogenase gene expression facilitated the targeted deletion of adhE gene in C.t. The markerless adhE gene deletion was done by double homologous recombination following the selection and counter-selection methods described previously.

Identification of riboswitch sequences in thermophilic bacteria:

The INFERNAL software was used in conjunction with shell scripts to search for 25 riboswitch covariance models against 73 representative thermophilic bacterial genomic sequences that were annotated as complete genomes in the NCBI nucleotide database and most of which were included in the well curated NCBI RefSeq database. The genomes were downloaded from the NCBI web-portal as a multi-fasta file and split into individual fasta files for each of the genomes using a Biopython script. Awk and other shell scripts were developed in-house to analyze the output from the INFERNAL software. This analysis indicated which of the 25 types of riboswitches in the riboswitch covariance model database were present in the chosen representative thermophilic bacteria and the relative frequencies/percentages of the different types of riboswitches in these bacteria.

The complete alignment of the RFAM Purine Riboswitch family (RF00167) was provided by RFAM researchers at EBI (European Bioinformatics Institute). Shell scripts were used to process the complete alignment to yield a tabulated and annotated version of the complete purine riboswitch alignment. The tabulated and annotated complete purine riboswitch alignment was next processed using an in-house Python script to identify the frequency of the four possible ribonucleotides at three functionally key positions (22, 51 and 74) from an aptamer region in the purine riboswitches. This investigation revealed that the most functionally significant conserved position (74) in the purine riboswitches was devoid of the Uracil ribonucleotide in thermophilic organisms. This Uracil ribonucleotide is a signature of adenine riboswitches which in turn indicates that adenine riboswitches are absent in thermophiles.

Quantification of Fermentation Products:

One milliliter of a culture was centrifuged and the supernatant was filtered through a 0.22 μM membrane. Fermentation products including ethanol, acetic acid, and lactic acid were measured by HPLC (1200 series; Agilent Technologies, Santa Clara, Calif.) with a mobile phase of 4 mM sulfuric acid (flow rate of 0.6 ml/min) using an Aminex HPX-87H column with a Micro Guard Cation H Cartridge. The column temperature was set to 55° C.

Disclosed herein is an analysis of riboswitch distribution in thermophilic bacteria, which indicates their significance in regulatory roles in thermophilic bacteria. The reporter assay rapidly characterizes riboswitch activity at elevated temperatures and serve as a platform to assess rationally engineered synthetic riboswitches activity. Inexpensive and finely tunable gene expression enables basic studies of a given species and its control of gene expression. The results disclosed herein are the first inducible and repressible gene regulatory systems using low-cost orthogonal inducers and repressors in thermophiles including *C. thermocellum*.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

Other objects, advantages, and novel features of the present invention will become apparent from the following detailed description of the invention when considered in conjunction with the accompanying drawings.

What is claimed is:

1. A non-naturally occurring riboswitch selected from the group consisting of a nucleotide sequence that is greater than 90% identical to SEQ ID NO: 1 or greater than 90% identical to SEQ ID NO: 3 wherein the non-naturally occurring riboswitch is operably linked to a heterologous promoter wherein the non-naturally occurring riboswitch is capable of regulating the expression of a gene of interest in a non-naturally occurring thermophilic organism.

2. The non-naturally occurring riboswitch of claim 1 wherein the riboswitch is capable of regulating the expression of a gene of interest at temperatures greater than 50 degrees Celsius.

3. The non-naturally occurring riboswitch of claim 1 wherein the expression of the gene of interest is downregulated.

4. The non-naturally occurring riboswitch of claim 1 wherein the expression of the gene of interest is upregulated.

5. The non-naturally occurring riboswitch of claim 4 wherein the gene of interest is expressed up to 29-fold over wild-type expression.

6. The non-naturally occurring riboswitch of claim 1 wherein the gene of interest is adhE.

* * * * *

SEQUENCE LISTING

```
<160> NUMBER OF SEQ ID NOS: 5

<210> SEQ ID NO 1
<211> LENGTH: 279
<212> TYPE: DNA
<213> ORGANISM: Thermoanaerobacterium saccharolyticum

<400> SEQUENCE: 1
attgtgtcag gacaagtaaa taatagctca tataattctg agaatacggc tcagaagtct      60
ctaccagaca accgtaaatt gtctgactat gagtgaaagt gtacctgagg gttccagcct     120
tattgtccat gtgtagaaaa cagtaaaggc gttcggaccg agcggtacag gcattgtatt     180
gccacacctg tgggataaaa gcccgggagg ataggtttca ctctatgtgt tggaatctat     240
cattccgggc ttgtttattt ttaaaattcg tttttattt                            279

<210> SEQ ID NO 2
<211> LENGTH: 279
<212> TYPE: DNA
<213> ORGANISM: Thermoanaerobacterium saccharolyticum

<400> SEQUENCE: 2
attgtgtcag gacaagtaaa taatagctca tataattctg agaatacggc tcagaagtct      60
ctaccagaca accgtaaatt gtctgactat gagtgaaagt gtacctgagg gttccagcct     120
tattgtccat gtgtagaaaa cagtaaaggc gttcggaccg agcggtacag gcattgtatt     180
gccacacctg tgggataaaa gcccgggagg ataggtttca ctctatgtgt tggaatctat     240
cattccgggc ttgtttattt ttaaaattcg tttttattt                            279

<210> SEQ ID NO 3
<211> LENGTH: 156
<212> TYPE: DNA
<213> ORGANISM: Bacillus subtilis
```

```
<400> SEQUENCE: 3
ggaaacgaat caattaaata gctattatca cttgtataac ctcaataata tggtttgagg      60
gtgtctacca ggaaccgtaa aatcctgatt acaaaatttg tttatgacat tttttgtaat    120
caggattttt tttatttatc aaaacattta agtaaa                              156

<210> SEQ ID NO 4
<211> LENGTH: 156
<212> TYPE: DNA
<213> ORGANISM: Bacillus subtilis

<400> SEQUENCE: 4
ggaaacgaat caattaaata gctattatat tttgtataac ctcaataata tggtttgagg      60
gtgtctacca ggaaccgtaa aatcctgatt acaaaatttg tttatgacat tttttgtaat    120
caggattttt tttatttatc aaaacattta agtaaa                              156

<210> SEQ ID NO 5
<211> LENGTH: 156
<212> TYPE: DNA
<213> ORGANISM: Bacillus subtilis

<400> SEQUENCE: 5
ggaaacgaat caattaaata gctattaaat tttgtataac ctcaataata tggtttgagg      60
gtgtctacca ggaaccgtaa aatcctgatt acaaaatttg tttatgacat tttttgtaat    120
caggattttt tttatttatc aaaacattta agtaaa                              156
```